United States Patent
Parker et al.

(10) Patent No.: US 11,240,890 B2
(45) Date of Patent: *Feb. 1, 2022

(54) CONTROLLING PHYSIOLOGICAL CONDITIONS BY CONTROLLING ENVIRONMENTAL CONDITIONS

(71) Applicant: Soraa, Inc., Fremont, CA (US)

(72) Inventors: Jeffery Robert Parker, Pleasanton, CA (US); Laszlo Andrew Takacs, Fremont, CA (US); Aurelien J. F. David, San Francisco, CA (US)

(73) Assignee: ECOSENSE LIGHTING, INC., Los Angeles, CA (US)

( * ) Notice: Subject to any disclaimer, the term of this patent is extended or adjusted under 35 U.S.C. 154(b) by 152 days.

This patent is subject to a terminal disclaimer.

(21) Appl. No.: 16/390,716

(22) Filed: Apr. 22, 2019

(65) Prior Publication Data

US 2019/0320516 A1   Oct. 17, 2019

Related U.S. Application Data

(63) Continuation of application No. 15/135,287, filed on Apr. 21, 2016, now Pat. No. 10,271,400.

(Continued)

(51) Int. Cl.
*H05B 45/20* (2020.01)
*A61B 5/0205* (2006.01)
(Continued)

(52) U.S. Cl.
CPC ......... *H05B 45/20* (2020.01); *A61B 5/02055* (2013.01); *A61B 5/318* (2021.01);
(Continued)

(58) Field of Classification Search
CPC ........................... H05B 45/20; A61B 2503/20
(Continued)

(56) References Cited

U.S. PATENT DOCUMENTS 8,038,615 B2 * 10/2011 Gobeyn ................. A61B 5/411
                                                              600/300
8,740,413 B1   6/2014 Krames
(Continued)

OTHER PUBLICATIONS

Unpublished U.S. Appl. No. 14/531,545, filed Nov. 2014, titled "System and Method for Providing Color Light Sources in Proximity To Predetermined Wavelength Conversion Structures".
(Continued)

*Primary Examiner* — Md Azad
(74) *Attorney, Agent, or Firm* — Fisherbroyles LLP

(57) ABSTRACT

In one embodiment, a method comprising: (a) receiving a set of physiological data associated with at least one health condition of an animal subject; (b) receiving a set of environmental data associated with one or more environment conditions to which the subject is or has been exposed; (c) determining a set of operating parameters for at least one environmental device based at least partially on at least a portion of the set of physiological data and at least a portion of the set of environmental data; and (d) transmitting the set of operating parameters to the at least one environmental device to at least partially control at least one controlled environmental condition to which the subject is exposed to thereby at partially control the at least one health condition.

19 Claims, 11 Drawing Sheets

Related U.S. Application Data

(60) Provisional application No. 62/150,669, filed on Apr. 21, 2015.

(51) Int. Cl.

| | | |
|---|---|---|
| *H05B 47/155* | (2020.01) | |
| *A61B 5/318* | (2021.01) | |
| *A61B 5/369* | (2021.01) | |
| *A61B 3/11* | (2006.01) | |
| *A61B 5/103* | (2006.01) | |
| *A61B 5/021* | (2006.01) | |
| *A61B 5/024* | (2006.01) | |
| *A61B 5/0531* | (2021.01) | |
| *A61B 5/00* | (2006.01) | |
| *A61B 5/01* | (2006.01) | |
| *A61B 5/1455* | (2006.01) | |
| *A61B 5/24* | (2021.01) | |
| *A61B 5/375* | (2021.01) | |

(52) U.S. Cl.
CPC ........... *A61B 5/369* (2021.01); *H05B 47/155* (2020.01); *A61B 3/112* (2013.01); *A61B 5/0071* (2013.01); *A61B 5/0077* (2013.01); *A61B 5/01* (2013.01); *A61B 5/021* (2013.01); *A61B 5/024* (2013.01); *A61B 5/0531* (2013.01); *A61B 5/1032* (2013.01); *A61B 5/1455* (2013.01); *A61B 5/24* (2021.01); *A61B 5/375* (2021.01); *A61B 5/4806* (2013.01); *A61B 5/4857* (2013.01); *A61B 2503/20* (2013.01); *A61B 2560/0242* (2013.01)

(58) Field of Classification Search
USPC ........................................................ 700/276
See application file for complete search history.

(56) References Cited

U.S. PATENT DOCUMENTS

| | | | |
|---|---|---|---|
| 9,289,622 B2 | 3/2016 | Feng | |
| 9,488,324 B2 | 11/2016 | Shum | |
| 10,192,033 B2 * | 1/2019 | Kurtz | ................. G06F 19/3418 |
| 2012/0289789 A1 * | 11/2012 | Jain | ...................... A61B 5/4848 |
| | | | 600/301 |
| 2014/0309790 A1 | 10/2014 | Ricci | |
| 2015/0035680 A1 | 2/2015 | Li | |
| 2015/0355649 A1 | 12/2015 | Ovadia | |
| 2016/0061472 A1 | 3/2016 | Lee | |
| 2016/0091217 A1 | 3/2016 | Verberkt | |
| 2017/0053068 A1 | 2/2017 | Pillai | |
| 2017/0192406 A1 * | 7/2017 | Ashdown | ............. G05B 19/042 |
| 2019/0290201 A1 * | 9/2019 | Greenwald | ............. A63B 71/10 |

OTHER PUBLICATIONS

Stefani et al., Evaluation of Human Reactions on Displays with LED Backlight and a Technical Concept of a Circadian Effective Display, SID 10 Digest, ISSN 0097-966X/10/4102-1120, 2010, 4 pgs.

* cited by examiner

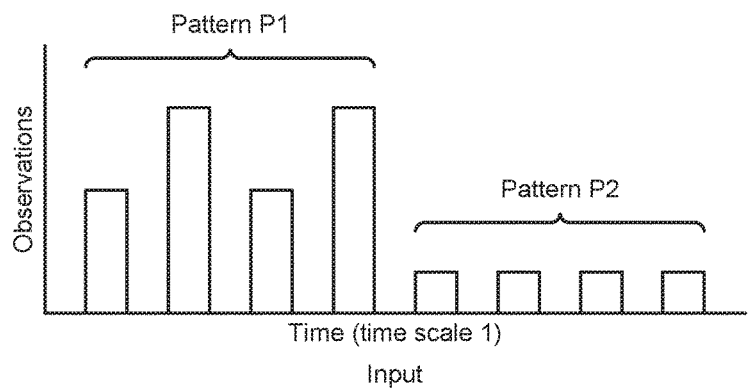
FIG. 1D1
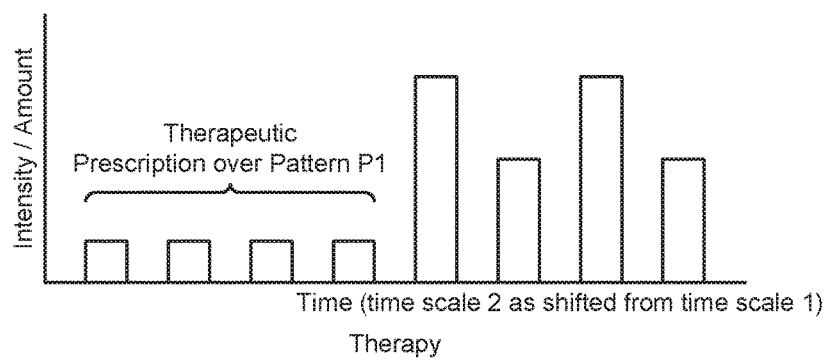
FIG. 1D2
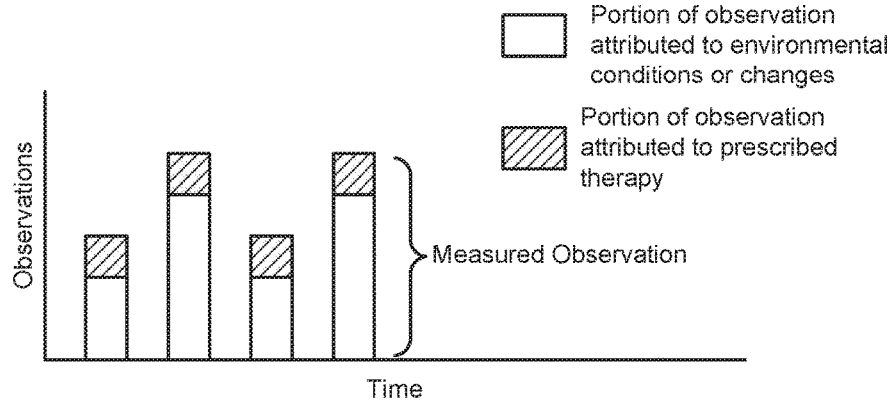
FIG. 1D3

CONTROLLING PHYSIOLOGICAL CONDITIONS BY CONTROLLING ENVIRONMENTAL CONDITIONS

REFERENCE TO RELATED APPLICATION

This application is a continuation of U.S. application Ser. No. 15/135,287, filed Apr. 21, 2016, which claims the benefit of U.S. Provisional Application No. 62/150,669, filed, Apr. 21, 2015, and hereby incorporated by reference.

FIELD

This disclosure relates generally to controlling physiological conditions by controlling environmental conditions, and, more particularly, to techniques for controlling environmental conditions affecting circadian biorhythms using real-time biometrics.

BACKGROUND

Light entering the eye has been discovered not only to facilitate vision, but also to cause various non-visual biological effects. For example, certain studies have revealed that environmental light is the primary stimulus for regulating circadian rhythms, seasonal cycles, and neuroendocrine responses. In some cases, and in particular with regard to biological responses to light, the environment can be controlled (e.g., to add more or less blue light) for various purposes. For example, light near the blue portion of the light spectrum can be used as a therapeutic tool in the treatment of sleep disorders and Seasonal Affective Disorders (SAD), such as "winter depression." In such cases, the exposure to short wavelength light in the range of 440 to 480 nm can be controlled to suppress the melatonin secretion by the pineal gland and affect the circadian rhythm.

Conventional techniques for environmental controls, however, generally fail to consider the state and changes of state of a subject and/or the subject's environment. For example, a factory with a night shift might add more blue light to stimulate physiological response (i.e., to keep workers alert and productive). However, such environmental controls fail to consider the real-time response of the subjects to the changing environmental conditions.

Therefore, approaches are needed to address the problem of observing a particular subject's physiological conditions, and modifying the environmental conditions in response to the observed aspects. The present invention fulfills this need, among others.

SUMMARY

The following presents a simplified summary of the invention in order to provide a basic understanding of some aspects of the invention. This summary is not an extensive overview of the invention. It is not intended to identify key/critical elements of the invention or to delineate the scope of the invention. Its sole purpose is to present some concepts of the invention in a simplified form as a prelude to the more detailed description that is presented later.

Some embodiments of the present disclosure address observing a particular subject's environmental and physiological conditions, and modifying the environmental conditions in response to the observations. Other embodiments are directed to approaches for making biometric observations and analyzing them so as to recommend or make changes to environmental conditions using biorhythm feedback signals. A particular embodiment is disclosed for controlling environmental conditions affecting circadian biorhythms using real-time biometrics.

Accordingly, one aspect of the invention is a method, which, in one embodiment comprises: (a) receiving a set of physiological data associated with at least one health condition of an animal subject; (b) receiving a set of environmental data associated with one or more environment conditions to which the subject is or has been exposed; (c) determining a set of operating parameters for at least one environmental device based at least partially on at least a portion of the set of physiological data and at least a portion of the set of environmental data; and (d) transmitting the set of operating parameters to the at least one environmental device to at least partially control at least one controlled environmental condition to which the subject is exposed to thereby at partially control the at least one health condition.

Another aspect of the invention is system, which, in one embodiment comprises: a processor; and memory operatively connected to the processor and configured to instruct the processor to execute the following steps: (a) receiving a set of physiological data associated with at least one health condition of an animal subject; (b) receiving a set of environmental data associated with one or more environment conditions to which the subject is or has been exposed; (c) determining a set of operating parameters for at least one environmental device based at least partially on at least a portion of the set of physiological data and at least a portion of the set of environmental data; and (d) transmitting the set of operating parameters to the at least one environmental device to at least partially control at least one controlled environmental condition to which the subject is exposed to thereby at partially control the at least one health condition.

Yet another aspect of the invention is a computer-readable medium, which, in one embodiment comprises a medium configured with the following instructions for execution by a processor: (a) receiving a set of physiological data associated with at least one health condition of an animal subject; (b) receiving a set of environmental data associated with one or more environment conditions to which the subject is or has been exposed; (c) determining a set of operating parameters for at least one environmental device based at least partially on at least a portion of the set of physiological data and at least a portion of the set of environmental data; and (d) transmitting the set of operating parameters to the at least one environmental device to at least partially control at least one controlled environmental condition to which the subject is exposed to thereby at partially control the at least one health condition.

Further details of aspects, objectives, and advantages of the disclosure are described below and in the detailed description, drawings, and claims. Both the foregoing general description of the background and the following detailed description are exemplary and explanatory, and are not intended to be limiting as to the scope of the claims.

BRIEF DESCRIPTION OF THE DRAWINGS

The drawings described below are for illustration purposes only. The drawings are not intended to limit the scope of the present disclosure.

FIG. 1D1, FIG. 1D2, and FIG. 1D3, depict techniques for reducing forms of therapeutic bias.

FIG. 2 shows a system for controlling environmental conditions affecting circadian biorhythms using real-time biometrics, according to some embodiments.

DETAILED DESCRIPTION

Figure 1A:
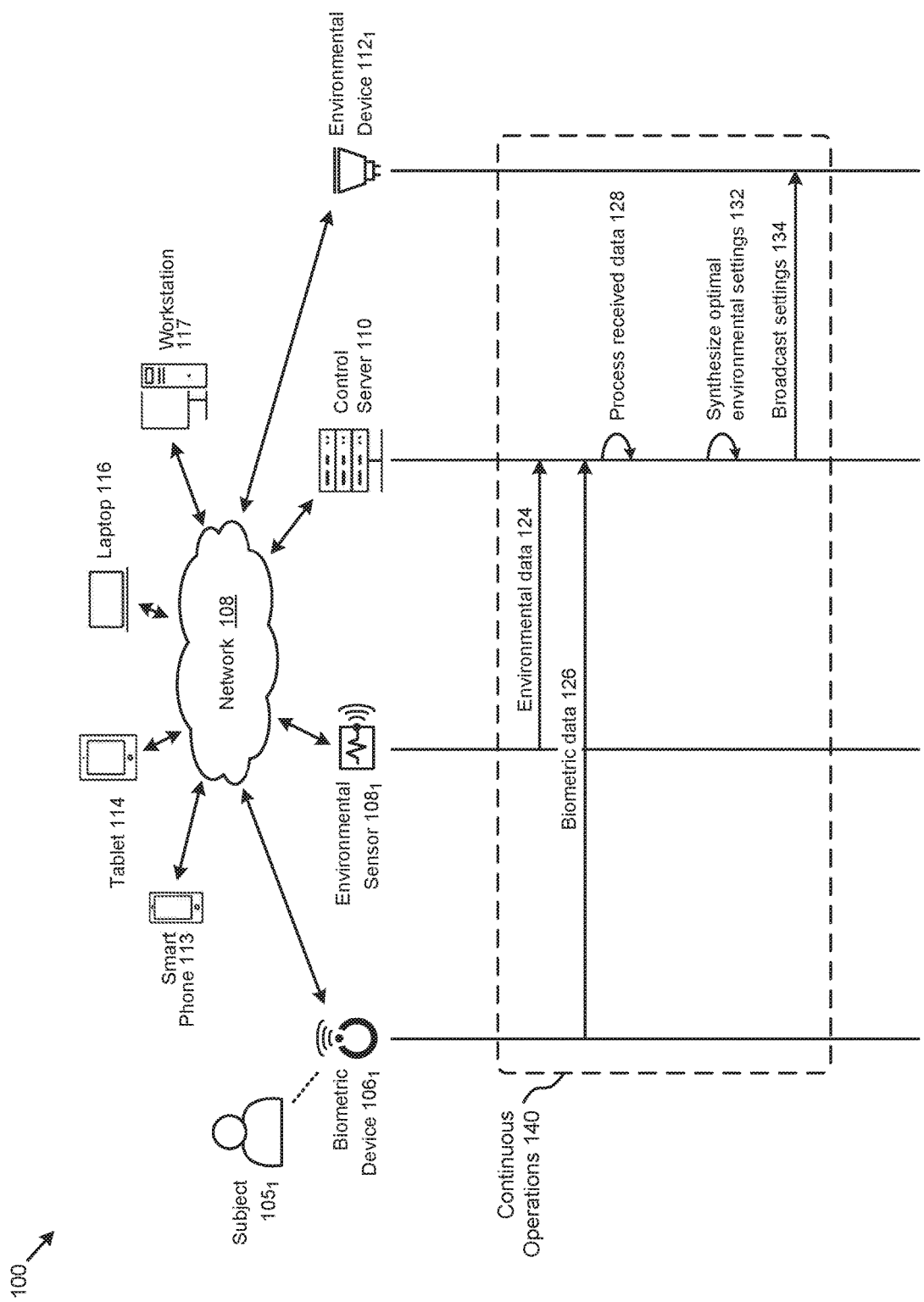
FIG. 1A depicts an environment in which embodiments of the present disclosure can operate.

The present invention relates generally to observing a particular subject's past and/or current environmental and physiological conditions, and modifying the environmental conditions to which the subject is exposed to control a health condition of the subject in response to the observed environmental and physiological conditions. In one embodiment, the system is configured to receive a set of physiological data associated with at least one health condition of an animal subject and a set of environmental data associated with one or more environment conditions to which the subject is, has been or will be exposed. Next, the system determines a set of operating parameters for at least one environmental device based at least partially on at least a portion of the set of physiological data and at least a portion of the set of environmental data. The system then transmits the set of operating parameters to the at least one environmental device to at least partially control at least one controlled environmental condition to which the subject is exposed to thereby at partially control the at least one health condition. These elements are discussed in detail below and in connection with different embodiments.

Although this application describes the invention in terms of the subject being a human, it should be considered that the invention may be applied to other animals, such as, for example, farm animals (e.g., cows and chickens) to increase productivity, or ranch animals (e.g., cattle) to decrease anxiety in processing facilities.

As used herein, a health condition refers to a property of an animal body capable of measurement, including, for example, body temperature, pulse, electrical activity of the heart (as measured, for example, by electrocardiogram (ECG)), electrical activity of the brain (as measured, for example, by an electroencephalogram (EEG)), activity of motor neurons (as measured, for example, by electromyography (EMG)), blood pressure, pupil dilatation, skin conductance, skin color, blood oxygenation, saliva and blood constituent levels—e.g., sugar, insulin, cholesterol, hormones (e.g. melatonin, cortisol, thyroid stimulating hormone, prolactin, serotonin, adrenalin, dopamine, gastrin, growth hormone, insulin, estrogen, progesterone, testosterone, etc.), white blood cell count, iron, etc., or any combination of one or more of the aforementioned conditions. In some embodiments, of particular interest are measurable conditions that are indicative (either directly or indirectly) of the circadian cycle, herein referred to as measurable circadian cycle indicative conditions (MCCICs). Many of the conditions above are MCCICs, including, for example, body temperature, pulse, pupil dilation, and relative levels of certain hormones, such as melatonin, and the interrelations of these conditions. As used herein, MCCIC also includes circadian cycle indicative conditions discovered or developed in the future.

As used herein, a set of physiological data includes one or more measurements of at least one health condition of an animal body. The set of physiological data can range from just one datum to many data. The measurement of these health conditions is well known and will not be considered in detail here. Suitable methods to acquire biometrics data comprise direct readings through a sensor in contact with the subject (body temperature/heart beat sensor), remote detection techniques (thermal imaging, remote radar such as Doppler radar and others, movement sensors), measurement of assays (blood/saliva . . . ), direct contact bio-chemical measurements (through a measuring device connected to the body, such as a chip pinned to a finger the collects hormone or glucose level) etc. The biometric data may be acquired by dedicated sensors, or by sensors which are attached to another device (for instance, a peripheral to a computer system/smart device, or a 'smart' accessory attached to a domestic appliance such as a light source). Smart snap accessories are known in the art and disclosed for example in U.S. Pat. No. 9,488,324, hereby incorporated by reference.

Generally, although not necessarily, it is preferable for the health condition measurement to be simple and noninvasive, and to avoid the need for assays or other consumable materials for performing the measurement. For example, although melatonin may be measured using the subject's saliva or blood as mentioned above, it is generally preferred that the relative circadian state be determined indirectly through more readily determined, conditions such as, for example, pulse temperature and pupil dilation. Obviously, as new measurement techniques are developed for internal properties, such as body chemistry (e.g., blood/saliva constituents), there may be a preference for measuring hormones and the like directly.

As specific examples of biometric measurements, the color of the skin of the subject (in a specific part of the body) may be measured by an optical sensor. A simple example of optical sensor is a camera (such as a charge-coupled device-CCD) such as the camera embarked on smartphones and other devices. In some cases, the optical measurement is performed under a known light source, so that the measurement can be interpreted with high accuracy (indeed, it is commonly easier to infer the color of an object when using a known light source rather than having to infer both the color of the object and the color of the light source). For instance, an embarked light-emitting diode (LED) source may be used for illumination when the optical measurement is performed. A simple example of such light source is the flash unit found on smartphones and other devices; another example is the screen of smart devices—which can for instance be set to emit white light with a known spectrum.

Besides a standard RGB (red, green, and blue spectrum) camera (such as that of a smartphone), other optical measurement devices can be employed. For instance, rather than three color sensors (red, green, blue), more sensors may be used in order to get more information on the reflectance spectrum of the measured object (such as the skin of the subject). We refer to such sensors (with more than three spectral channels) as "spectrometers". In some embodiments a spectrometer is implemented by combining a standard CCD sensor (such as that of a camera) with a diffraction grating. Then CCD can be used for measuring a spectrum. This conversion from camera to spectrometer may be done on-the fly—either automatically or manually. In some embodiments, a spectrometer system can be calibrated at first by a direct measurement of a known light source, or a direct measurement of a known object illuminated by a known light source. For instance, the light emitted by a flash LED (or by a display screen) may be shined on a white wall or a mirror and measured with the spectrometer to calibrate the spectrometer's response. After this, the spectrometer may be used for spectral and reflectance measurements.

In another example, an additional biosensor is used to measure the amount of melatonin in the subject (for instance in his saliva) in order to gain further information on his circadian cycle. Other hormones and chemicals can likewise be measured. The measurement can be performed by collecting a biological sample and measuring in a separate setup, or by a bio-reading system attached to the subject.

In another example, pupil dilation is measured. This can, for instance, be measured by a dedicated system, or by a simple imaging technique on a smart device (i.e. imaging of the user's eye by a smartphone camera under illumination by the phone's flash light).

In addition, health conditions may include medical assessments of a subject's health by a doctor, or a medical test.

As used herein, environmental conditions are measurable conditions of the environment to which the subject animal was exposed, is exposed, or will be exposed. For example, environmental conditions may include temperature, time, time zone, location of the animal, presence of the animal, duration of the presence of the animal, humidity, wind, wind chill, precipitation, barometric pressure, sun rise and sun set, dew point, tides, smog index/air quality, Ultraviolet (UV) index, sound/noise, and light exposure, diet, drug intake, or any combination of one or more of the aforementioned conditions. Light exposure is a broad term that relates to the type and intensity of the light received by the animal. The type of light is typically, although not necessarily, related to the spectral power distribution (SPD), which, specifically, is a measurement describing the power per unit area per unit wavelength of an illumination (radiant exitance), and, more generally, refers to the concentration, as a function of wavelength, of any radiometric or photometric quantity may relate to spectrum. Of particular interest herein, is exposure of the animal to the blue light spectrum, which is connected with influencing the circadian cycle as described above. Other light spectrums that may be monitored, include, for example, ultraviolet light and infrared light. In addition to the SPD emitted by a light source or the diffuse SPD in a given environment, other measures of interest may include optical quantities (SPD, radiance, irradiance) at a specific point or in a specific direction, for instance entering the subject's pupil or impinging on the subject's skin.

The set of environment data corresponds to one or more measures of at least one environmental condition mentioned above. The set of environmental data can range from just one datum to many data. The measurement of the environmental conditions above using environment sensors is well known and will not be considered herein in detail.

Some embodiments of the invention address the need for quantifying a stimulus received by a human subject. For instance, there may be a need to monitor the amount of light received by a subject over a period of time (which may span hours, days, weeks, months or other periods of times). Further, there may be a need to measure other quantities related to light exposure. This includes the spectrum of the light, its CCT, its color rendering, etc. Embodiments of the invention comprise a device with an optical sensor, which is worn by the subject; as the subject is exposed to light, the sensor records data pertaining to exposure. This data can be accumulated over time to estimate the light exposure of the subject. This data can be used in a computer system to influence the circadian stimulation of the subject.

These measurements of a property of light may be coupled with other measurements, including biometric measurements. For instance, a biometric device may measure the body temperature of a subject, oxygen levels in their blood, bodily levels of hormones, etc. These measurements may be correlated with the light measurements, for instance to draw an inference on an aspect of the patient's health.

In various embodiments, the light-sensing devices are placed at a known position relative to the subject's body so that their light reading can be interpreted quantitatively. In some embodiments, the light sensor is often or always exposed to light—for instance, it may be desirable to place the sensor on a watch or other wearable, rather than on a phone, which may be placed in a pocket. In other embodiments, the sensor is placed on a computer on which the user is working—for instance an office computer.

In a specific example, the subject wears a smart watch, which comprises several optical sensors—including a spectrometer. The sensors measure the intensity and spectrum of the ambient light. Since the watch has a known position on the body, the measurements can be interpreted to measure how much light the subject receives over time, and how much of this light is in a spectral range stimulating the circadian system (for instance, illuminance in the range 430-490 nm). Periodically, a sensor is also used to measure the reflectance spectrum of the skin of the user's arm—this is performed by directing the spectrometer towards the arm, emitting light from the watch's screen and collecting the reflected light from the arm with the spectrometer sensor. Further, the watch measures the wrist skin's temperature. The information on ambient light, temperature and skin reflectance is then combined by a computer system to infer an aspect of the patient's health or circadian cycle. Based on this data, an amount of circadian stimulation is determined over the course of a day. Specifically, this amount is used by a computer system to determine a necessary amount of supplementary light required by the subject. Accordingly, at a later time, the subject receives a specific dose of light with a specific circadian stimulation level from a light source, which is part of the embodiment.

In some embodiments of the invention, such measurements are used to calibrate information on the subject. For instance, biometrics may be collected over a period of time to obtain a baseline about the subject. This baseline may be related to various aspects of health, including aspects of the circadian rhythm (this includes sleep patterns, levels of hormones related to the circadian cycle etc. . . . ). Likewise, light exposure may be collected over a period of time to characterize the subject's habits or typical environment. Once a baseline is established, deviations from the baseline can be measured (either to monitor drift in the subject's condition, or to assess his response to a treatment). Subject-specific calibration may be desirable because baseline biometric signals may vary significantly from individual to individual; therefore, it may not be possible to interpret biometric readings in the absence of an initial calibration phase. Any of the aforementioned calibration techniques can be used singly or in combination, and can be used together with techniques to assess and remove therapeutic bias from measured observations (e.g., see FIG. 1D).

A controllable environmental condition refers to the above-mentioned environmental conditions that can be controlled, at least in part, by an environmental device.

An environmental device is a device that at least in part controls a controllable environmental condition. Examples of environmental devices, include, for example, lighting devices, HVAC components (e.g. thermostats, air conditioners, furnaces, heaters, air purifiers, fans and other air handling devices), humidifiers, dehumidifiers, sound systems (e.g., speakers and noise cancelling apparatus), and shade or shutter controls, or any combination of one or more of the aforementioned conditions. Of particular interest herein are lighting devices, which can be used for a variety of lighting applications, including, for example, ambient lighting, spot light and backlighting of display screens. In one embodiment, the lighting devices are configured to control the type and/or intensity of the light emitted. Such lighting devices are known and are disclosed for example in U.S. patent application Ser. No. 14/531,545, hereby incorporated by reference.

It should be noted that the measurements of environmental conditions and health conditions can be contemporaneous, historical, or anticipatory (i.e. predictive). Additionally, the measurements may be based on a short sampling period, e.g., immediate/a few seconds, or they may be based on a longer sampling period—e.g. hours, days, weeks, months or years. For example, in one embodiment, the exposure to light may be measured over hours, while temperature may be measured instantaneously. For example, in some embodiments, the health conditions are used to determine the instant health state of the subject (for instance whether the heart rate or another biometric is within a specified range), or the history of the health state of the subject (amount of exercise over a period, level of a hormone such as melatonin over time, evolution of body temperature, etc.). In the latter case the historical health condition may span a time of a few minutes (sudden change in biometrics), a few hours (light exposure throughout the day, diet throughout the day) or several days (sleep cycle and travel over days and weeks). One of skill in the art will understand the appropriate term for recording the measurement for the given application in light of this disclosure. Future environmental conditions may for instance be obtained as an input from the user (plans to be in a specific location, travel plan, diet plants). Future health conditions may be inferred from a model (predetermined model, machine-learning model . . . ) which may take current/past health and environmental conditions as data.

Determining the operating parameters typically comprises using a simple algorithm. For example, the algorithm may compare the set of physiological data and the set of environmental data to one or more predetermined limits and then using logic operators based on the comparison to establish the operating parameters for the at least one environmental device. For example, if the melatonin level is below a certain limit and the exposure to blue is above a certain limit, then set the operating parameters to reduce the dose of blue light to a certain limit to induce the production of melatonin. In this example, the logical operators of "if/then", "greater than," "less than," and "and" were used to determine the operating parameters. Those of skill in the art will readily understand how to determine operating parameters using logical operators in light of this disclosure.

Machine learning may be used in a variety of embodiments to establish or refine the algorithm. Machine learning may be based on large data sets (e.g. data relating environmental conditions and health conditions, as know from healthcare studies), on the inputs described above (health and environmental conditions), and on other specific knowledge about the subject. Examples of machine learning techniques include neural networks, Bayesian inference and other methods known in the art.

Generally, although not necessarily, the system and method of the present invention, determines a target controllable environmental condition and then determines the operating parameters to achieve the target. The environmental device is configured to receive the operating parameters, and adjust or otherwise generate an output according to the operating parameters to reach the controllable environmental condition. Although a target controllable environmental condition may be used, it is not necessary. For example, in some embodiments, the operating parameters are determined by trial and error to achieve a target health condition of the subject. This may be done without knowing or measuring the actual controllable environmental condition being controlled. In other embodiments, the controllable environmental condition is explicitly measured and a feedback loop may be used to adapt the parameters of the environmental device.

The herein disclosed embodiments address the aforementioned problem by receiving environmental data from an environment (e.g., location, temperature, barometric pressure, lighting conditions, spectral content of ambient light, etc.) and physiological data from a subject (e.g., pulse rate, blood-oxygen level, blood-sugar level, melatonin level, etc.), processing the data, and using a learning model to determine an optimal set of environmental parameters and settings to broadcast to a set of environmental devices that can affect the environmental conditions. The techniques can continually receive new data, and synthesize and broadcast new environmental settings in real time to enable systems for controlling environmental conditions affecting circadian biorhythms using real-time biometrics.

For example, in one embodiment, from inferences on the health state of a subject, an algorithm may prescribe a desired change to environmental conditions. For instance, if the circadian cycle of the subject is out-of-phase, a light therapy can be provided (increase of blue light and of light intensity to entrain the circadian cycle, or paucity of blue light and reduced intensity to reduce circadian stimulation). In another example, the temperature and humidity of the ambient air are tuned to affect the subject's body temperature. A closed-feedback loop may be used between health conditions and environmental conditions.

Various embodiments include controllable light sources so that the subject is exposed to a given amount of light with a given spectrum at a given time in order to influence his circadian cycle. For instance, if it has been determined that the subject has not received enough circadian-stimulating blue light in the first few hours of the day, he may be exposed to a large amount of blue light from a computer screen mid-morning to compensate for this. Conversely, if it has been determined that the user has received excessive amounts of circadian-stimulating blue light throughout the day, lights can be automatically dimmed or tuned to a spectrum containing less blue light (including a low-CCT spectrum, or a standard CCT spectrum with very little blue light and violet light instead to achieve a desired chromaticity) at night.

Reference is now made to certain embodiments shown in the figures. The disclosed embodiments are not intended to be limiting of the claims.

Figure 1B:
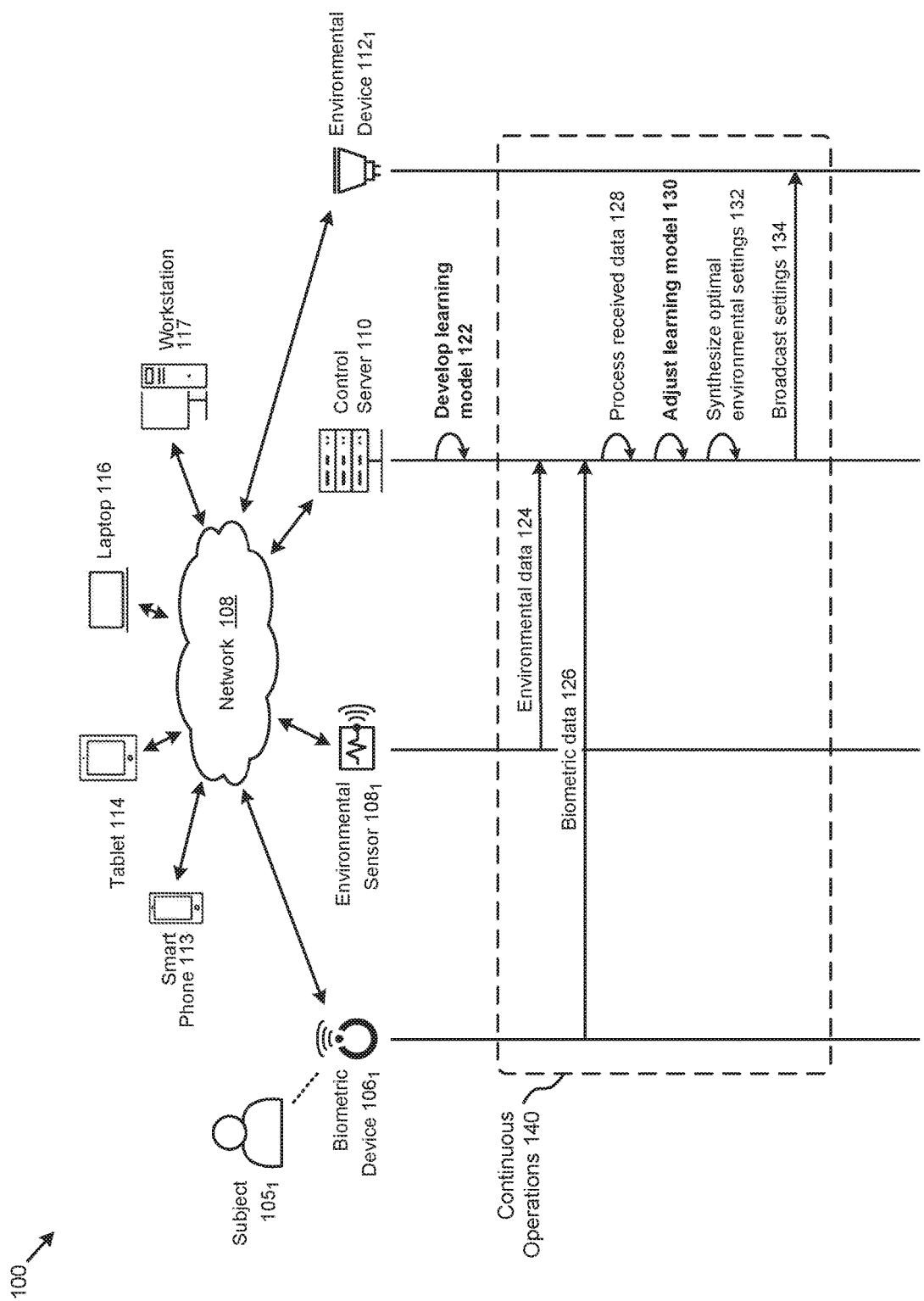
FIG. 1B depicts an environment in which embodiments of the present disclosure can operate.

FIG. 1A and FIG. 1B depict operations within environment 100. As shown in FIG. 1A, environment 100 comprises various computing systems (e.g., servers and devices) interconnected by a network 108. The network 108 can comprise any combination of a wide area network (e.g., WAN), local area network (e.g., LAN), wireless network, cellular network, wireless LAN (e.g., WLAN), or any such means for enabling communication of computing systems. The network 108 can also be referred to as the Internet. More specifically, environment 100 comprises at least one instance of a control server 110, an instance of a biometric device $106_1$ (e.g., smart watch, wristband monitor, etc.) worn by a subject $105_1$, an instance of an environmental sensor $108_1$ (e.g., motion detector, temperature sensor, etc.), and an instance of an environmental device $112_1$ (e.g., light modulating device, overhead troffer, ambient luminaires, task lighting, standalone orb, etc.). In one or more embodiments, information detected by the biometric device $106_1$ and the environmental sensor $108_1$ can be received by the control server 110 and used to control the environmental device $112_1$. In some cases, the control server 110 can control other light modulating devices, such as a smart phone 113, a tablet 114, a laptop 116, and the display of a workstation 117.

As shown, the control server 110, the biometric device $106_1$ for measuring a health condition, the environmental sensor $108_1$ for measuring an environment condition, and the environmental device $112_1$ for controlling a controllable environmental condition, can exhibit a set of high-level interactions (e.g., operations, messages, etc.). In this embodiment, the shown high-level interactions can represent interactions in systems for controlling environmental conditions affecting circadian biorhythms using real-time biometrics. More specifically, a learning model for determining desired environmental conditions based, in part, on a subject's environmental and physiological state can be developed (e.g., trained, simulated, optimized, etc.) at the control server 110 (see operation 122 of FIG. 1B). The environmental sensor $108_1$ can send environmental data (see message 124) and the biometric device $106_1$ can send physiological data from the subject $105_1$ (see message 126) to the control server 110 for processing. For example, the environmental data represents environmental observations detected by the environmental sensor $108_1$ (e.g., location, temperature, barometric pressure, lighting conditions, spectral content of ambient light, etc.), and the physiological data represents biometric observations detected by the biometric device $106_1$ (e.g., pulse rate, blood-oxygen level, blood-sugar level, melatonin level, etc.). The control server 110 can process (e.g., filter, adjust, translate, etc.) the received data (see operation 128) and validate and/or make adjustments to the learning model as needed (see operation 130 of FIG. 1B). Using the updated learning model and the current environmental and physiological data, an optimal set of environmental parameters and settings can be determined (see operation 132) and broadcast to the environmental device $112_1$ and other devices (see message 134). As shown, the control server 110 can continually receive new data, and synthesize and broadcast new environmental settings in real time (see continuous operations 140). One embodiment of a system for implementing the techniques shown in FIG. 1A and disclosed herein is shown in FIG. 2.

Figure 1C:
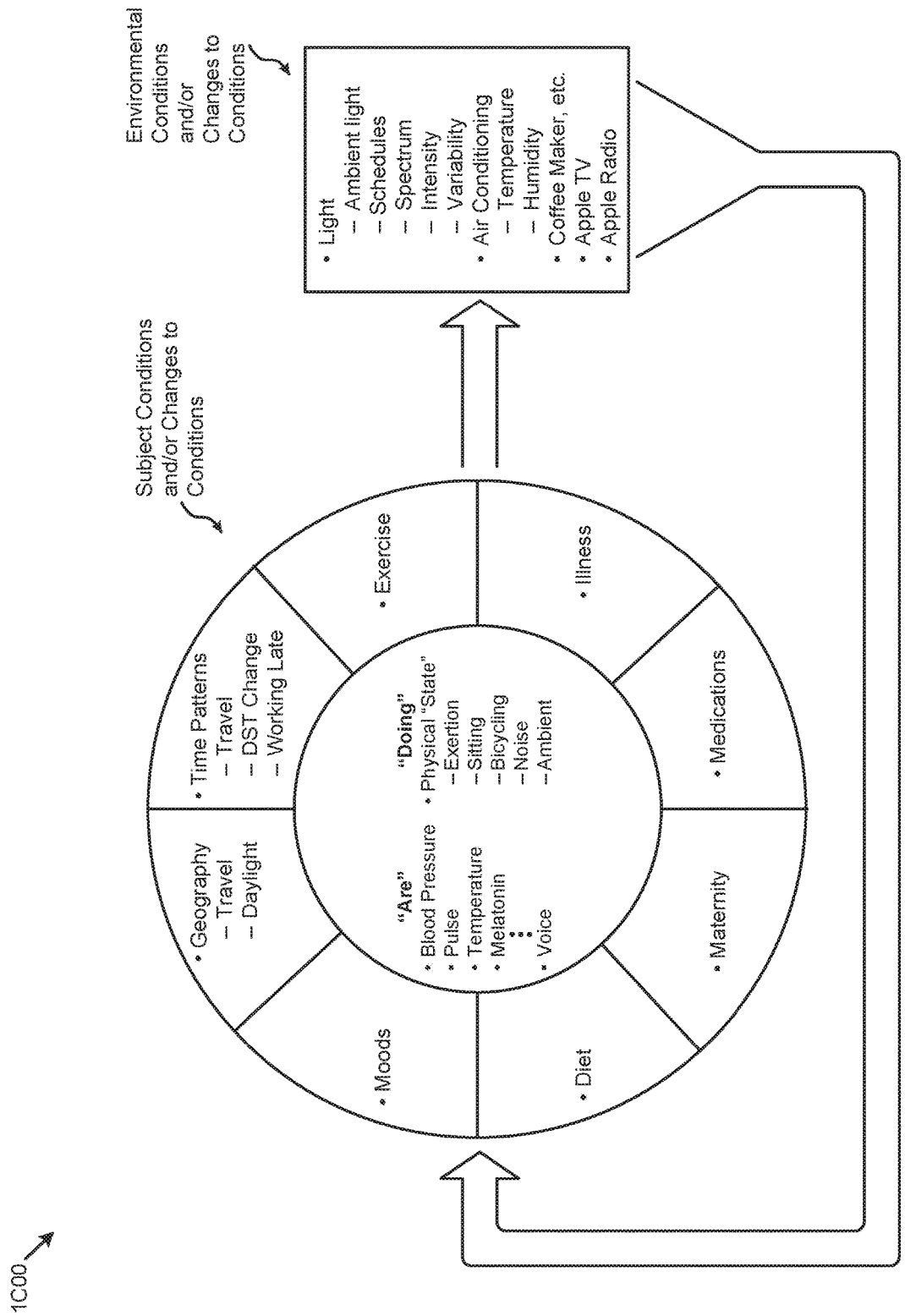
FIG. 1C depicts a feedback path between bio-factors and environmental conditions, according to some embodiments.

FIG. 1C depicts a feedback path 1C00 between biofactors and environmental conditions. The shown subject conditions include passive states (e.g., see "Are") as well as active states (see "Doing"). The subject conditions are used to effect environmental conditions or changes to environmental conditions so as to effect a therapy, or in other control a health condition of the subject. The therapy can include blue light therapies (e.g., reduction or increase in blue light) that are facilitated by violet-emitting LEDs.

FIG. 1D1, FIG. 1D2, and FIG. 1D3, depict techniques for reducing forms of therapeutic bias. The aforementioned therapies can cause changes in the subject, and such changes can be included in measurements taken (for example) using biometric devices. When incorporating feedback (e.g., measured responses in the subject, determining patterns, etc.), the new measurements can include the effect of the therapy. Such effects can sometimes be included in the new measurements as a therapeutic bias. Such biases can be calculated and removed, for example, prior to delivering new observations to the learning model. In some cases a pattern can be identified and/or a change in patterns can be identified, and the therapy can be prescribed so as to counteract undesired effects of a pattern or to counteract undesired effects of changes in a pattern. This is illustrated in FIGS. 1D1-1D3. In a first phase, a pattern P1 of an input observation (which could be biometric and/or environmental data) is collected (D1), and a constant (for instance) amount of a therapeutic dose is administered (D2); the impact on a biometric factor of interest are measured (D3) and is broken down into two components: one stemming from the variation of input observation, and another from the therapeutic dose. Once this breakdown is established, in subsequent phase Pattern P2, therapeutic doses 1D2 are adapted to the input observations 1D1 so that the biometric factor 1D3 is maintained at a desired value.

Figure 2:
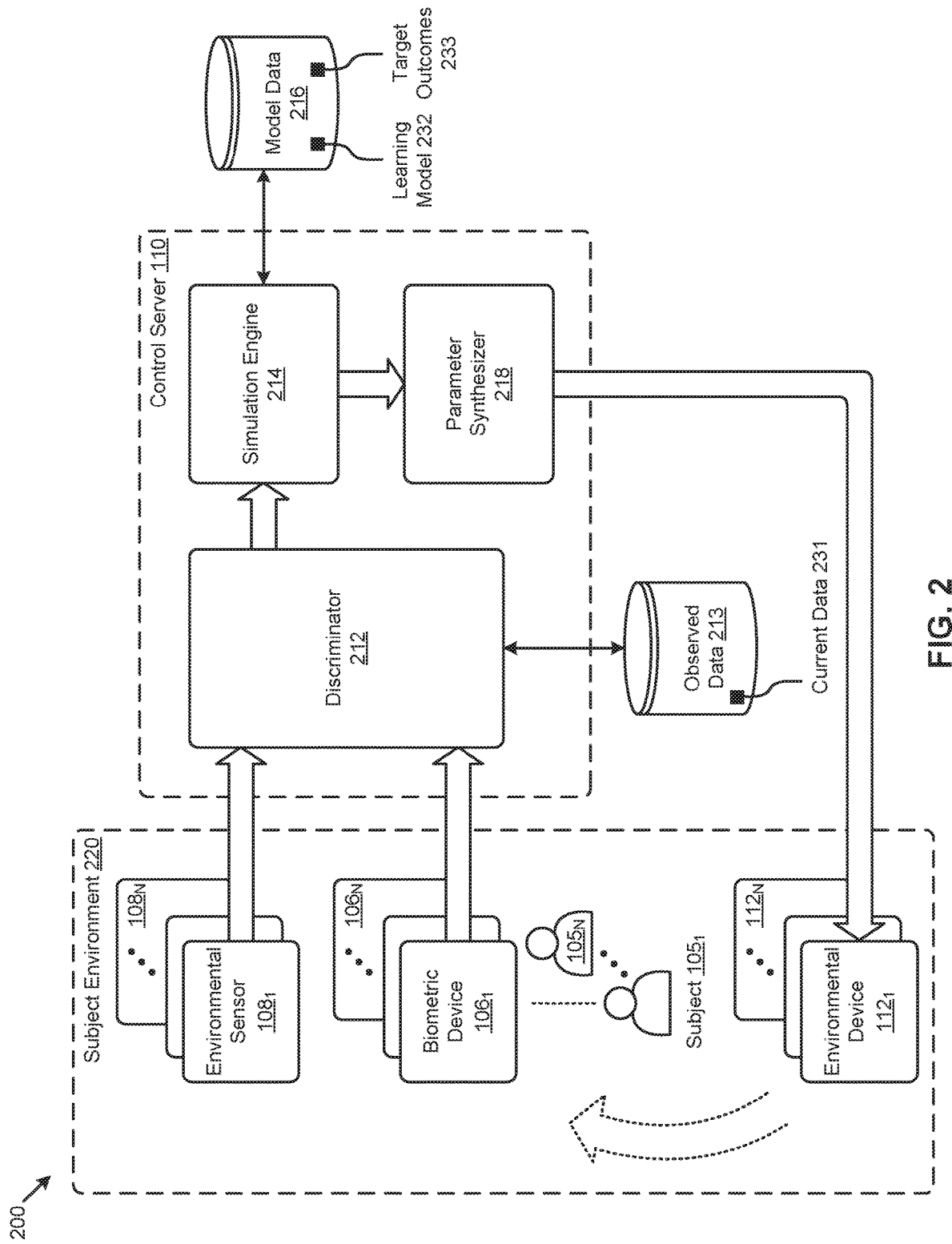

FIG. 2 shows one embodiment of a system 200 for controlling environmental conditions affecting circadian biorhythms using real-time biometrics. The system 200 shown in FIG. 2 presents an example embodiment of various modules for implementing the herein disclosed techniques, and operated by the control server 110 from FIG. 1A. The system 200 further comprises a subject environment 220 that includes a set of one or more environmental sensors (e.g., environmental sensor $1081_1$ to environmental sensor $108_N$), and a set of one or more biometric devices (e.g., biometric device $106_1$ to biometric device $106_N$) worn by a respective set of subjects (e.g., subject $105_1$ to subject $105_N$). The subjects in the subject environment 220 are exposed to conditions determined, in part, by a set of environmental devices (e.g., environmental device $112_1$ to environmental device $112_N$). As shown in system 200, a discriminator 212 can receive data (e.g., over the network 108) from the environmental sensors and biometric devices, and can process (e.g., filter, eliminate, adjust, translate, etc.) the received data to generate a statistically reliable set of current data 231 to be stored in the observed data 213. In some cases, periods of observations can be eliminated when the data is determined to potentially bias forward control calculations. A simulation engine 214 can use the current data 231 and other data (e.g., target outcomes 233) to develop and adjust a learning model 232 stored in a store of model data 216. The output of the simulation engine 214 is received by a parameter synthesizer 218 to convert to parameters and settings specific to the instances of the environmental devices that have been identified for adjustment. As an example, the discriminator 212 might receive data that indicates a subject has just arrived at a certain work area and needs additional lighting. The data might further indicate the subject has a high melatonin level (e.g., is sleepy). In this example, the simulation engine 214 can simulate the desired response to these inputs using the learning model to determine more ambient light with a higher blue light intensity is needed in the certain work area. The parameter synthesizer 218 can identify the environmental devices (e.g., IP address, device ID, etc.) and determine the device-specific settings (e.g., commands, etc.) to communicate to physically effect the desired response in real time. More details related to the operations of the components of the system 200 are described as pertains to FIG. 3A and FIG. 3B.

Figure 3A:
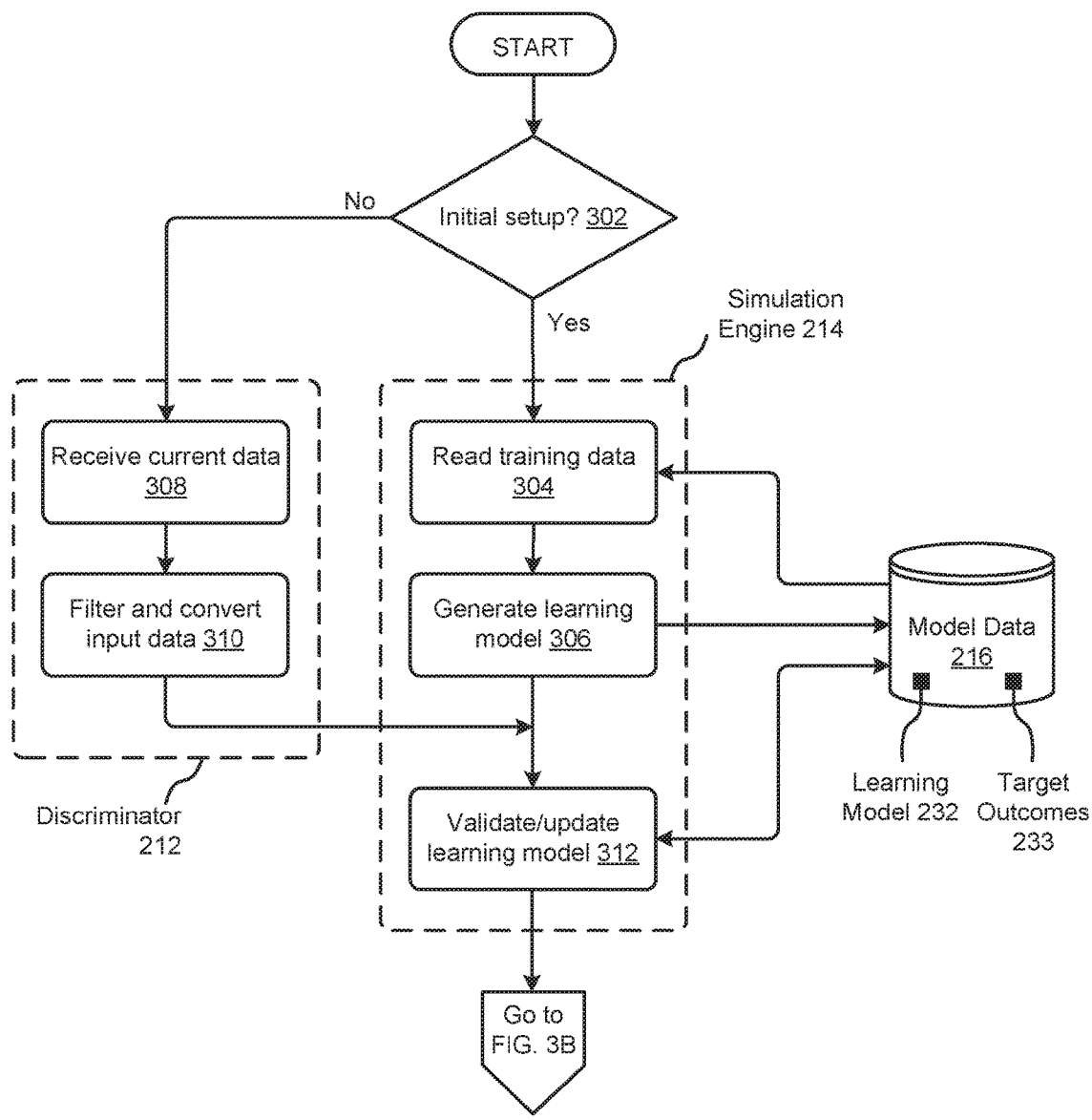
FIG. 3A depicts a learning model development flow as used in systems for controlling environmental conditions affecting circadian biorhythms using real-time biometrics, according to some embodiments.

FIG. 3A depicts a learning model 312 development flow 3A00 as used in systems for controlling environmental conditions affecting circadian biorhythms using real-time biometrics. The learning model development flow 3A00 shown in FIG. 3A comprises a set of operations that can be executed by the discriminator 212 and the simulation engine 214 described in FIG. 2. Additional or fewer steps, and/or other allocation of operations are possible. Specifically, the learning model development flow 3A00 can be used to develop, validate, and update a learning model used in systems for controlling environmental conditions affecting circadian biorhythms using real-time biometrics. More specifically, the learning model development flow 3A00 can start a determination of whether such a system is being initially setup (see decision 302). If this is an initial setup, the simulation engine 214 can read a set of training data from the model data 216 (see step 304). For example, the training data can include target outcomes 233, experimental data, expected conditions and biometrics, subject data, etc. Using the training data, a learning model (e.g., the learning model 232) can be generated (see step 306). For example, the learning model can comprise a set of mappings (e.g., linear, non-linear, logical, algorithmic, etc.) of input data (e.g., detected environmental and physiological data) to output data (e.g., environmental settings and parameters). If this is not an initial setup, the discriminator will receive a current set of data from the environmental sensors and biometric devices (see step 308), and filter and convert the received data for use by the simulation engine 214 (see step 310). For example, the discriminator 212 might receive an HTTP message from a smart sensor (e.g., "DID=1234") that requires parsing and extracting of the pertinent information (e.g., "temp=26.52"), and conversion to a syntax acceptable by the simulator (e.g., "did.1234.temp=26.52").

Figure 3B:
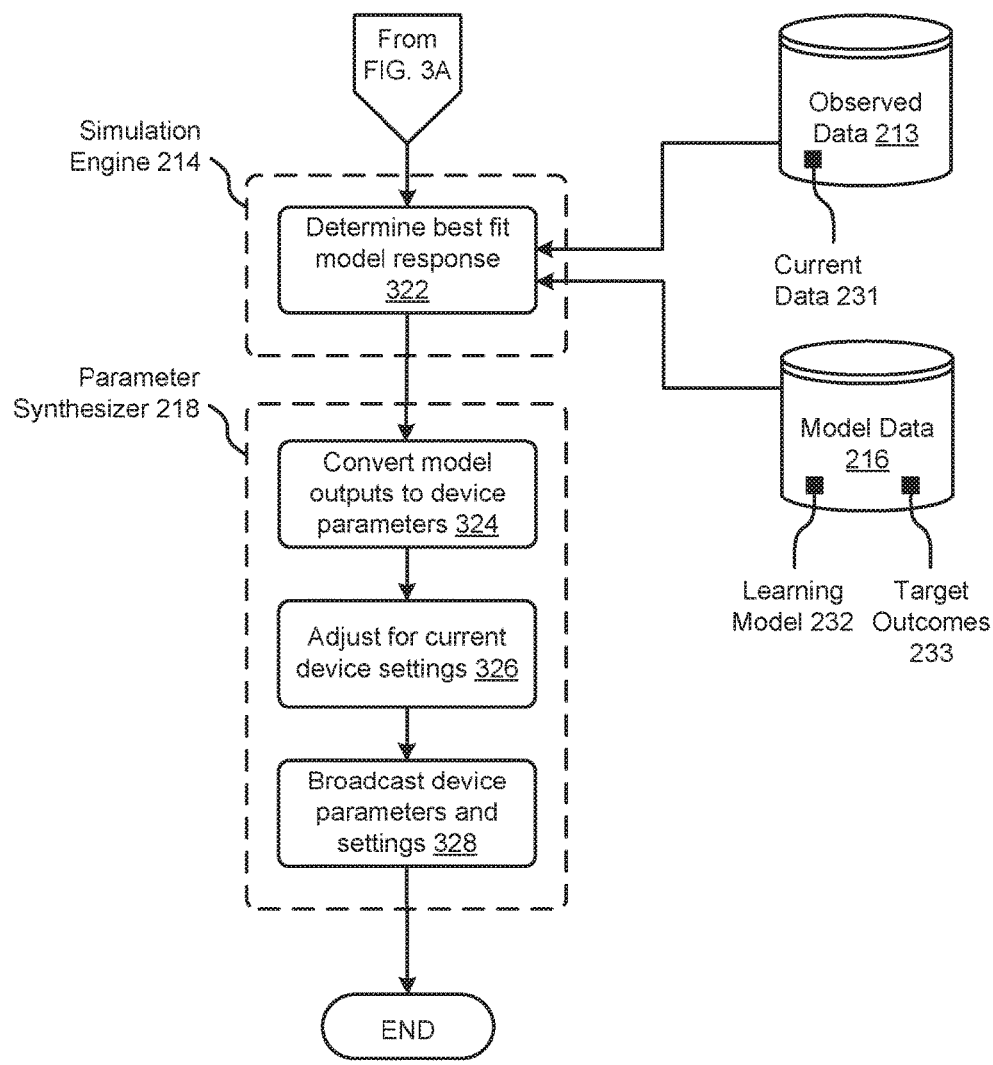
FIG. 3B depicts an environmental parameter synthesis flow as used in systems for controlling environmental conditions affecting circadian biorhythms using real-time biometrics, according to some embodiments.

FIG. 3B depicts an environmental parameter synthesis flow 3B00 as used in systems for controlling environmental conditions affecting circadian biorhythms using real-time biometrics. The environmental parameter synthesis flow 3B00 shown in FIG. 3B comprises a set of operations that can be executed by the simulation engine 214 and the parameter synthesizer 218 described in FIG. 2. Additional or fewer steps, and/or other allocation of operations are possible. Specifically, the environmental parameter synthesis flow 3B00 can be used to generate the device-specific parameters and settings 328 that will yield a set of environmental adjustments to optimally affect circadian biorhythms using real-time biometrics. More specifically, the environmental parameter synthesis flow 3B00 can continue from the process shown in FIG. 3A to determine a best fit model response to the current data 231 received from the environment and subject (see step 322). For example, the simulation engine 214 can use various techniques (e.g., sensitivity analyses, parameter sweeps, Monte Carlo analyses, etc.) to determine the response from the learning model 232 that best fits the target outcomes 233 given the current environmental and physiological conditions associated with the current data 231. The best fit model output is delivered to the parameter synthesizer 218 to convert to device-specific settings (see step 324). For example, the simulation engine 214 output might call for an increase in blue light in a designated work area, and the parameter synthesizer might then convert that output to a specific device (e.g., led lamp "led.1122") and a device-specific setting (e.g., "led.1122.b=7.85"). In some cases, the parameter synthesizer 218 can also adjust for current device settings (see step 326). For example, a given environmental device to be adjusted may be in a current state and/or at a current setting (e.g., at a range limit, a relative setting, etc.) that might affect the desired adjustment. When all device parameters and settings have been determined and adjusted, the parameter synthesizer can broadcast the updated control information in a format acceptable for each adjusted device. One embodiment and example of an implementation of the herein disclosed techniques is described as pertains to FIG. 4.

Figure 4:
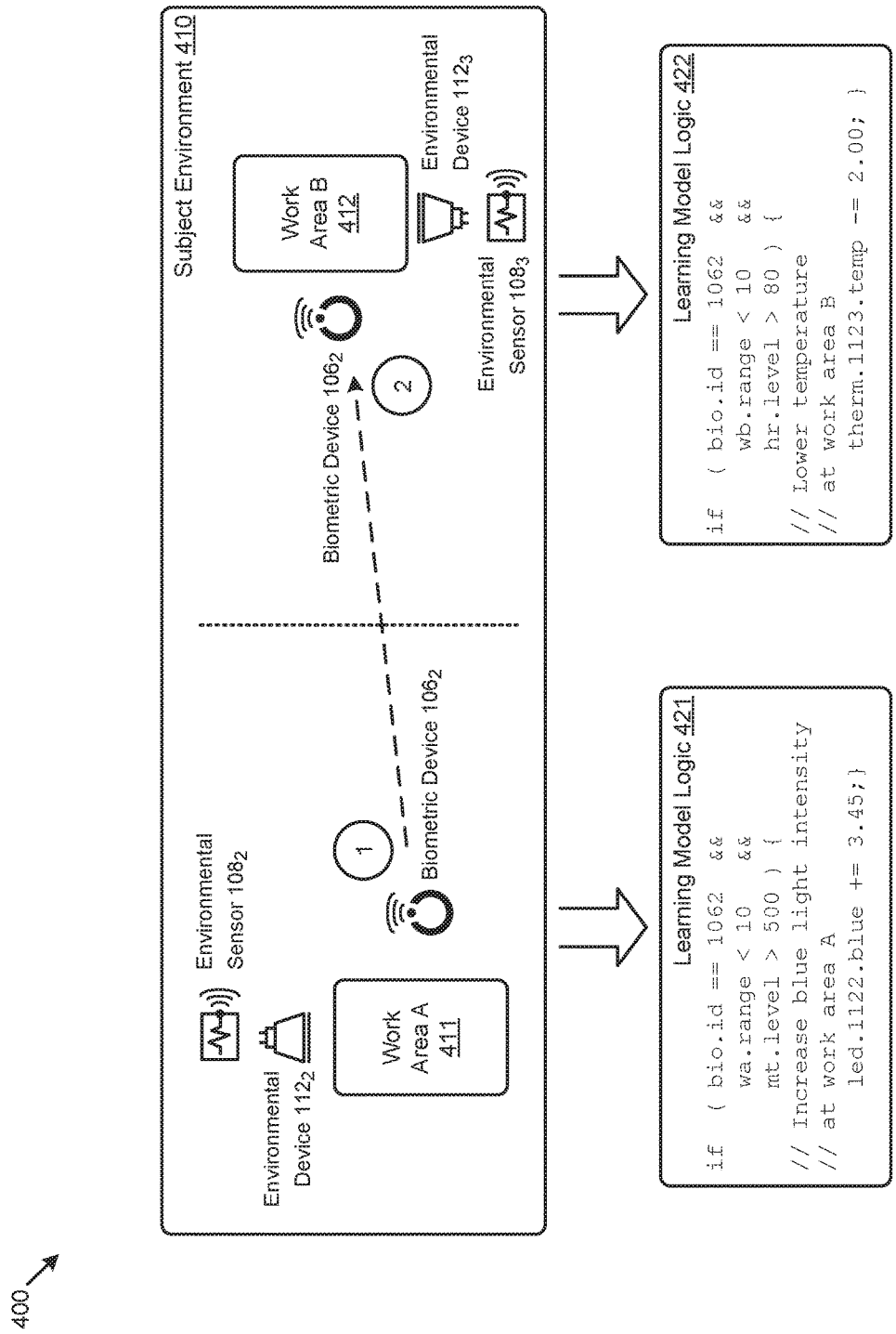
FIG. 4 is a visual representation of a light modulation technique as used in systems for controlling environmental conditions affecting circadian biorhythms using real-time biometrics, according to some embodiments.

FIG. 4 is a visual representation of one embodiment of a light modulation technique 400 as used in systems for controlling environmental conditions affecting circadian biorhythms using real-time biometrics. The light modulation technique 400 is implemented in a subject environment 410 that includes a work area A 411 in proximity of an environmental sensor $108_2$ (e.g., motion detector) and an environmental device $112_2$ (e.g., LED lamp). The representation further comprises a work area B 412 in proximity of an environmental sensor $108_3$ (e.g., motion detector) and an environmental device $112_3$ (e.g., thermostat). A subject wearing a biometric device $106_2$ (e.g., "bio.id=$106_2$") starts in a first position by work area A 411, and then moves to a second position by work area B 412. The light modulation technique 400 further depicts two examples of learning model logic: a learning model logic 421 and a learning model logic 422. Other types and implementations of learning model logic can be deployed in other examples and embodiments.

When in the first position, learning model logic 421 is processed (e.g., by the simulation engine 214). The learning model logic 421 shows that if the biometric device $106_2$ is within 10 feet of work area A 411 (e.g., as detected by environmental sensor $108_2$) and the subject's melatonin level is greater than 500 (index value or arbitrary units for relative comparison only) (e.g., as detected by the biometric device $106_2$), then the blue spectrum of environmental device $112_2$ should be increased by 3.45 μW/cm2. When the subject is in the second position, learning model logic 422 is processed (e.g., by the simulation engine 214). The learning model logic 422 shows that if the biometric device $106_2$ is within 10 feet of work area B 412 (e.g., as detected by environmental sensor $108_3$) and the subject's heart rate level is greater than 80 beats per minute (e.g., as detected by the biometric device $106_3$), then the temperature near work area B 412 should be decreased by 2.00° F. As shown, the herein disclosed approach implemented in the light modulation technique 400 illustrates the control of environmental conditions affecting circadian biorhythms using real-time biometrics.

In other examples, the learning model is based not only on an instantaneous biometric reading, but also on other data including: current environmental data (temperature in the room, light spectrum and level in the room . . . ), past biometric data (level of a hormone, heart rate, body temperature, physical exertion through the day), past environmental data (light level and spectrum, ambient temperature through the day). For example, in one embodiment, the dose of blue light received by the subject is measured throughout the day. In the evening, when the subject arrives home, the level of melatonin and body temperature are measured. Based on this environmental and biometric data, an algorithm determines the current level of circadian entrainment. Based on this determination, and on past historical data on the subject's living habits, a schedule of indoor light exposure is determined in order to control the circadian entrainment and bring the subject to a state of sleepiness at the desired time. For instance, if melatonin suppression is observed, the dose of blue light in the indoor environment is reduced to reduce circadian entrainment ('if melatonin< [determined level], reduce blue dose below [target level]). Further, the biometrics of the subject may be monitored through the night. The environmental conditions (such as temperature) may be adapted through the night in reaction with the subject's biometrics, for instance to improve sleep quality (room temperature may be tuned in response to the subject's body temperature). The sleep cycle may be monitored, and at a time that is adequate for wake-up (end of a sleep cycle that is close to a target wake-up time), lighting in the room is turned on and the blue dose is elevated to wake up the subject and synchronize his circadian phase.

In another example, the subject travels across time zones. The travel schedule is known. Based on readings of light exposure and biometrics, a light therapy is devised to shift the circadian clock of the subject over several days. In one embodiment, this done in anticipation of travel across time zones. For example, when traveling to an earlier time zone, in one embodiment, the therapy starts several days before the travel, for instance, a desired dose of blue light may be provided in the early morning to shift the circadian cycle to an earlier phase, in preparation for travel. Likewise, after returning from an earlier time zone, decreasing doses of blue light may be provided in the early morning to shift gradually the circadian cycle to an earlier phase, shifting the circadian clock by one or several hours each day.

Although the previous examples act on a contemporaneous time scale—influencing biological aspects over a few hours—the present invention applies to other therapeutic actions over a longer time scale. For instance, an environmental factor (light or other) may be controlled over a period of several days, weeks or months to have a desired health aspect.

Figure 5:
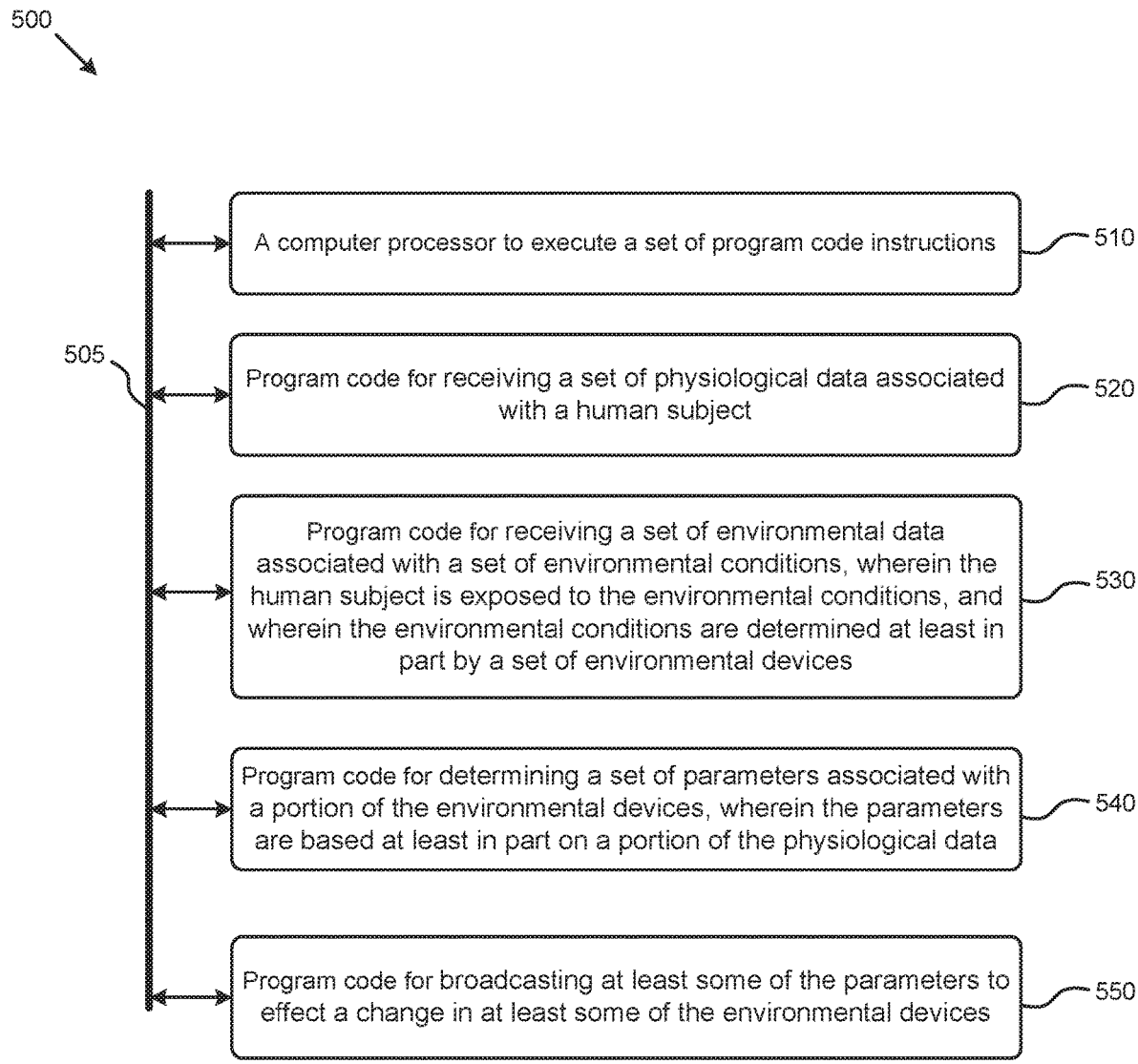
FIG. 5 is a block diagram of a system for controlling environmental conditions affecting circadian biorhythms using real-time biometrics, according to an embodiment.

FIG. 5 is a block diagram of a system for controlling environmental conditions affecting circadian biorhythms using real-time biometrics, according to some embodiments. The system 500 comprises at least one processor and at least one memory, the memory serving to store program instructions corresponding to the operations of the system. As shown, an operation can be implemented in whole or in part using program instructions accessible by a module. The modules are connected to a communication path 505, and any operation can communicate with other operations over communication path 505. The modules of the system can, individually or in combination, perform method operations within system 500. Any operations performed within system 500 may be performed in any order unless as may be specified in the claims. The shown embodiment implements a portion of a computer system, presented as system 500, comprising a computer processor to execute a set of program code instructions (see module 510) and modules for accessing memory to hold program code instructions to perform: using a computing system having at least one processor to perform a process, the process comprising; receiving a set of physiological data associated with a human subject (see module 520); receiving a set of environmental data associated with a set of environmental conditions, wherein the human subject is exposed to the environmental conditions, and wherein the environmental conditions are determined at least in part by a set of environmental devices (see module 530); determining a set of parameters associated with a portion of the environmental devices, wherein the parameters are based at least in part on a portion of the physiological data (see module 540), and broadcasting at least some of the parameters to effect a change in at least some of the environmental devices (see module 550).

In some embodiments, circadian rhythm control is sought to improve the sleep patterns of a subject. This is not always the case, however, Studies have shown that some cancerous cells are especially sensitive to the circadian clock, and that a properly-timed circadian clock disruption could selectively kill them (e.g. with higher sensitivity than healthy cells). In some embodiments, circadian clock control is employed as a form of cancer therapy.

Figure 6:
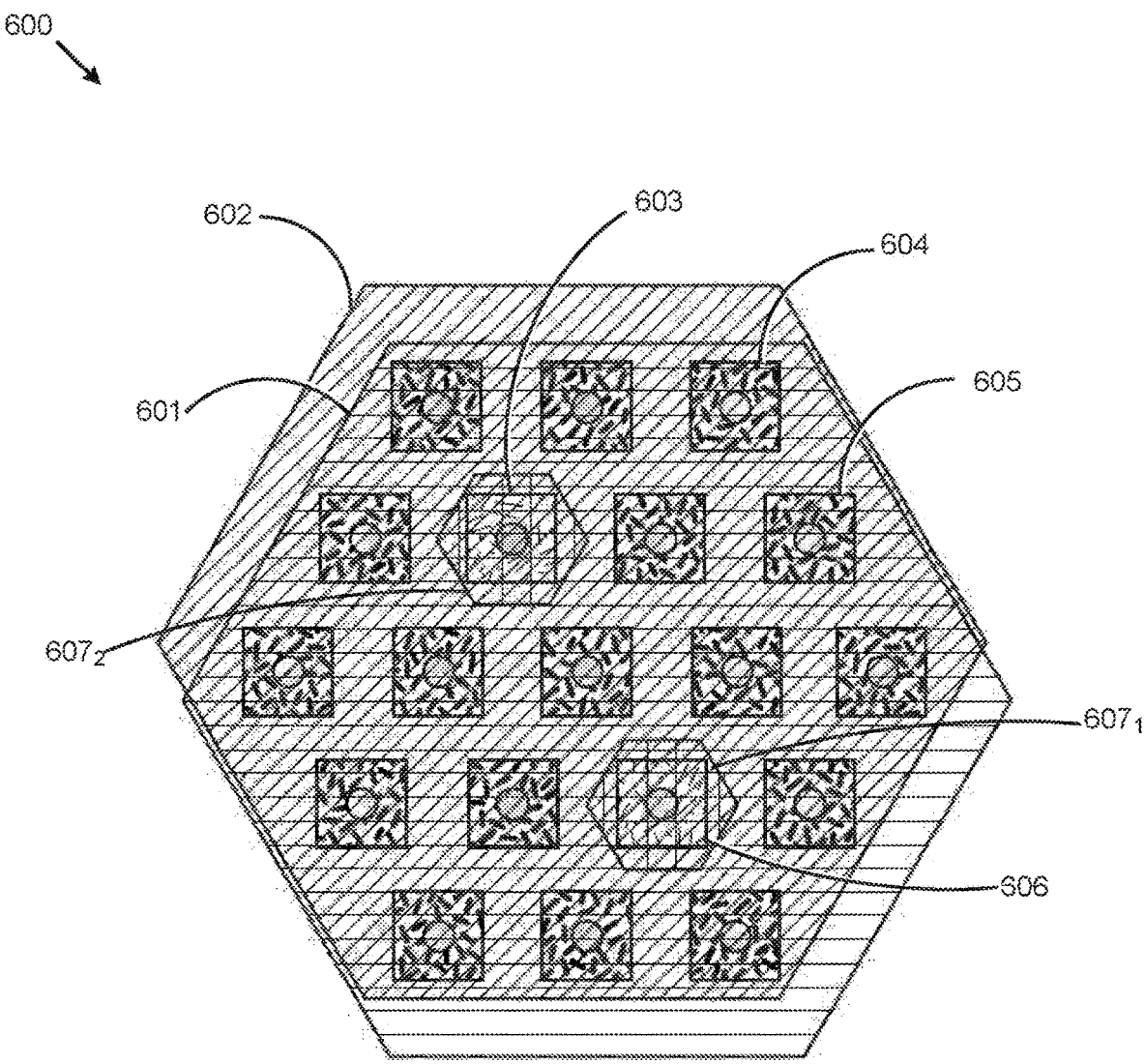
FIG. 6 is a simplified diagram illustrating an optical device, according to an embodiment of the present disclosure.

FIG. 6 is a simplified diagram illustrating an optical device 600, according to an embodiment of the present disclosure. As shown in FIG. 6, an optical device 600 includes a submount 111 (not shown) that has a surface. A number of radiation sources are provided on the submount. According to various embodiments, two types of radiation sources are provided, and each type of radiation source is associated with a range of wavelength. For example, radiation sources include a first plurality of radiation sources that are configured to emit radiation characterized by a first wavelength. More specifically, the first wavelength can have a range of between about 380 nm to 470 nm. In a specific embodiment, the first wavelength is characterized by a peak emission at about 420 nm to 470 nm. The first plurality of radiation sources are positioned on the surface. The first plurality of radiation sources have an n number of radiation sources. For example, the first plurality of radiation sources includes LED device 604 and LED device 605.

The radiation sources of optical device 600 also include a second plurality of radiation sources that are configured to emit radiation characterized by a second wavelength. In various embodiments, the second wavelength is shorter than the first wavelength. More specifically, the second wavelength is violet or ultraviolet. In a specific embodiment, the second plurality of radiation sources are characterized by a peak emission in the range of about 380 nm to about 430 nm. In certain embodiments, the second wavelength is less than 390 nm. The second plurality of radiation sources is positioned on the surface of the submount. The second plurality of radiation sources comprises m number of radiation sources. The ratio between m and n is predetermined based on a selected wavelength. Typically, n is greater than m. The ratio of n to m can be 1:1, 2:1, 10:1, and other ratios. For example, the ratio is based on a selected wavelength output for the optical device 500. As an example, the second plurality of radiation sources comprises short violet LED device 603 and short violet LED device 606.

In various embodiments, the arrangement of the radiation sources is patterned. More specifically, the locations of the second plurality of radiation sources are predetermined and are covered and/or surrounded by a specific phosphor pattern (e.g., phosphor pattern $607_1$, phosphor pattern $607_2$). The phosphor pattern is configured to be proximal to instances from among the second plurality of radiation sources. More specifically, the phosphor pattern is more remote from the first plurality of radiation sources. The phosphor pattern is configured to absorb at least a portion of radiation emitted by the second plurality of radiation sources. In various embodiments, the phosphor pattern is associated with a wavelength emission ranging from about 440 nm to about 490 nm. In a specific embodiment, the phosphor pattern comprises blue phosphor material. For example, the patterned blue phosphor material is used to convert violet or ultraviolet radiation to blue light. Among other things, the blue light converted by the patterned phosphor material can help create desired color balance and improve efficiency even while the intensity of the blue light is varied in accordance with blue light therapies.

Further details regarding general approaches to varying blue light for white light and for therapeutic purposes are described in U.S. Pat. No. 8,740,413 B1, which is hereby incorporated by reference in its entirety.

As shown, the optical device 600 also includes a first wavelength converting layer 601 configured to absorb at least a portion of radiation emitted by the first plurality of radiation sources and the second plurality of radiation sources. The first wavelength-converting layer is associated with a wavelength emission ranging from 590 nm to 650 nm. For example, the first wavelength-converting layer comprises red phosphor material that is adapted to emit substantially red color light.

The second wavelength converting layers 601 and 602 are configured to absorb at least a portion of radiation emitted by the first plurality of radiation sources and the second plurality of radiation sources. The second wavelength-converting layer is associated with a wavelength emission ranging from 490 mn to 590 nm. For example, the second wavelength-converting layer comprises a green phosphor that is adapted to emit substantially green light.

As an example, the first and second wavelength-converting layer can absorb radiation from both the first plurality and second plurality of radiation sources. Additionally, the first and second wavelength converting layers may also absorb emission from the phosphor pattern. It is to be appreciated that the embodiments of the present disclosure can provide efficiency gains over conventional techniques.

In one embodiment, a first plurality of radiation sources configured to emit radiation characterized by a first wavelength ranging from about 430 nm to about 480 nm, wherein the first plurality of radiation sources are positioned on the mounting surface and having n number of radiation sources that are situated in proximity to a second plurality of radiation sources configured to emit radiation characterized by a second wavelength shorter than the first wavelength. The second plurality of radiation sources are positioned on the mounting surface and having m number of radiation sources. The ratio between n and m can be predetermined based on a selected wavelength, or the effective ratio of light emitted from the first plurality of radiation sources with respect to the second plurality of radiation sources can be varied under therapeutic control.

For producing pleasing light, a wavelength-converting layer is positioned in an optical path of radiation of at least one of the first radiation sources, and the wavelength-converting layer is configured to absorb radiation at the first wavelength. In exemplary embodiments, the first wavelength-converting layer has an emission wavelength in the range from about 480 nm to about 600 nm.

Further variations are possible in the design of the light emitter. In some cases, the radiation sources are placed on a plurality of mounting members, rather than on a single submount or mounting member. For instance, a first set of LEDs emitting in a wavelength range 430-490 nm are placed on a first mounting member; and a second set of LEDs emitting in a wavelength range 400-430 nm are placed on a second mounting member.

In various embodiments, the invention comprises more than one radiation source and the radiation sources can be driven independently. For instance an embodiment may comprise a first set of sources controlled by a first driver and a second set of sources controlled by a second driver. These drivers may be modulated by a computer or other automated system according to embodiments of the invention, for instance in order to vary a circadian stimulation.

Further, the light source can be characterized by a number of measures quantifying the emitted light or the emitted spectral power distribution (SPD). This includes luminance, illuminance, radiation diagram, correlated color temperature (CCT), chromaticity, color rendering index (CRI) and other color rendition measures, fraction of the SPD in a given spectral range (such as 400-430 nm or 430-490 nm). These measures can be tuned dynamically, or can be kept at a given value, in accordance with embodiments of the invention. For instance, the CRI may be maintained above a desired value such as 80; the CCT may be varied within a desired range, such as from 3000K to 5000K; the fraction of the SPD in the range 430-490 nm may be varied from less than 0.1% to more than 20%. All these variations may be performed by tuning the emitted spectrum—for instance in embodiments of the invention having independent strings of LEDs, by varying the power in each string; in various embodiments this tuning is performed by a computer or other automated system.

Figure 7:
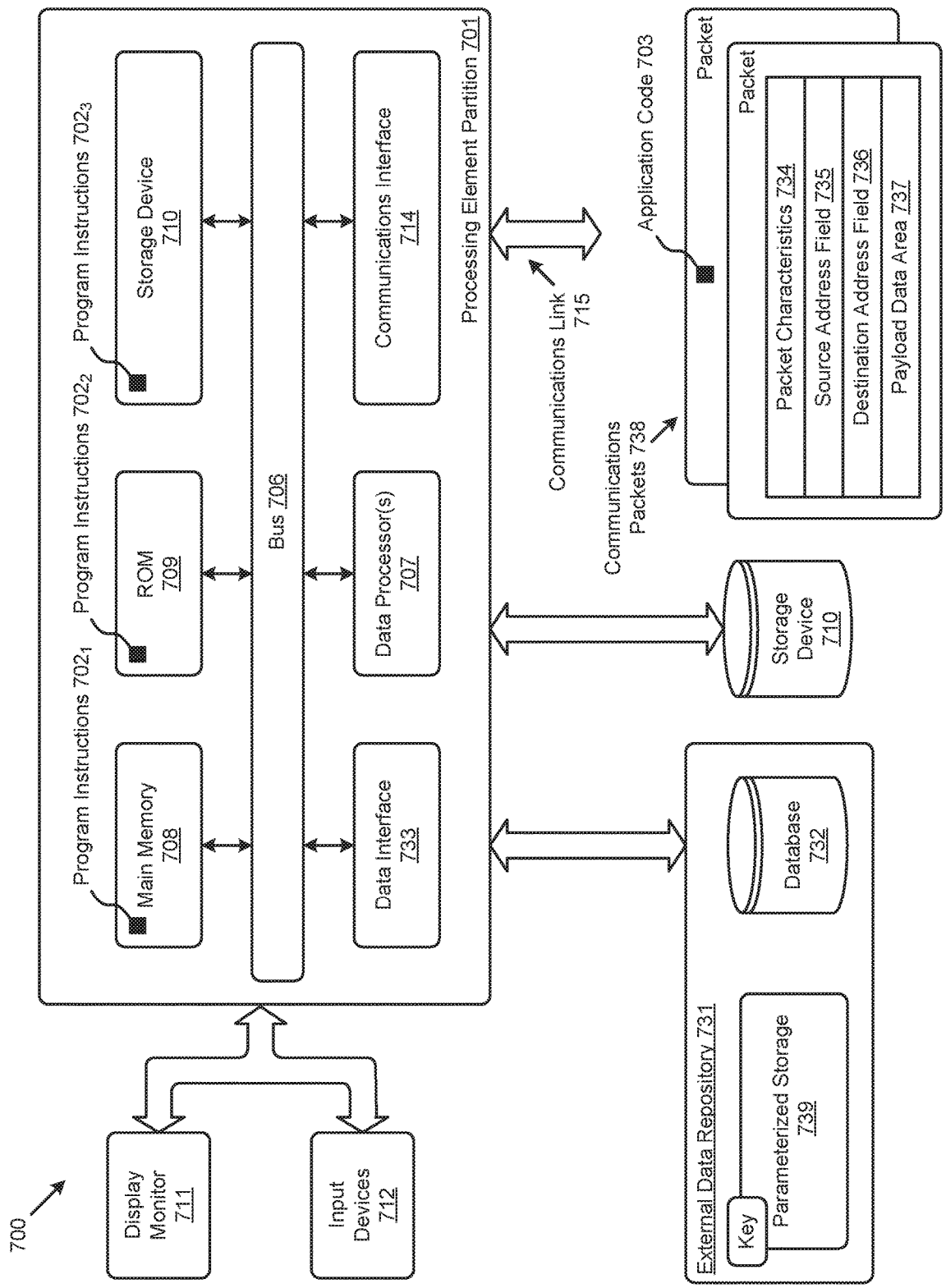
FIG. 7 depicts exemplary architectures of components suitable for implementing embodiments of the present disclosure and/or for use in the herein-described environments.

FIG. 7 depicts a block diagram of an instance of a computer system 700 suitable for implementing embodiments of the present disclosure. Computer system 700 includes a bus 706 or other communication mechanism for communicating information. The bus interconnects subsystems and devices such as a CPU, or a multi-core CPU (e.g., data processor 707), a system memory (e.g., main memory 708, or an area of random access memory RAM), a non-volatile storage device or non-volatile storage area (e.g., ROM 709), an internal or external storage device 710 (e.g., magnetic or optical), a data interface 733, a communications interface 714 (e.g., PHY, MAC, Ethernet interface, modem, etc.). The aforementioned components are shown within processing element partition 701, however other partitions are possible. The shown computer system 700 further comprises a display 711 (e.g., CRT or LCD), various input devices 712 (e.g., keyboard, cursor control), and an external data repository 731.

According to an embodiment of the disclosure, computer system 700 performs specific operations by processor 707 executing one or more sequences of one or more program code instructions contained in a memory. Such instructions (e.g., program instructions $702_1$, program instructions $702_2$, program instructions $702_3$, etc.) can be contained in or can be read into a storage location or memory from any computer readable/usable medium such as a static storage device or a disk drive. The sequences can be organized to be accessed by one or more processing entities configured to execute a single process or configured to execute multiple concurrent processes to perform work. A processing entity can be hardware-based (e.g., involving one or more cores) or software-based, and/or can be formed using a combination of hardware and software that implements logic, and/or can carry out computations and/or processing steps using one or more processes and/or one or more tasks and/or one or more threads or any combination therefrom.

According to an embodiment of the disclosure, computer system 700 performs specific networking operations using one or more instances of communications interface 714. Instances of the communications interface 714 may comprise one or more networking ports that are configurable (e.g., pertaining to speed, protocol, physical layer characteristics, media access characteristics, etc.) and any particular instance of the communications interface 714 or port thereto can be configured differently from any other particular instance. Portions of a communication protocol can be carried out in whole or in part by any instance of the communications interface 714, and data (e.g., packets, data structures, bit fields, etc.) can be positioned in storage locations within communications interface 714, or within system memory, and such data can be accessed (e.g., using random access addressing, or using direct memory access DMA, etc.) by devices such as processor 707.

The communications link 715 can be configured to transmit (e.g., send, receive, signal, etc.) communications packets 738 comprising any organization of data items. The data items can comprise a payload data area 737, a destination address 736 (e.g., a destination IP address), a source address 735 (e.g., a source IP address), and can include various encodings or formatting of bit fields to populate the shown packet characteristics 734. In some cases the packet characteristics include a version identifier, a packet or payload length, a traffic class, a flow label, etc. In some cases the payload data area 737 comprises a data structure that is encoded and/or formatted to fit into byte or word boundaries of the packet.

In some embodiments, hard-wired circuitry may be used in place of or in combination with software instructions to implement aspects of the disclosure. Thus, embodiments of the disclosure are not limited to any specific combination of hardware circuitry and/or software. In embodiments, the term "logic" shall mean any combination of software or hardware that is used to implement all or part of the disclosure.

The term "computer readable medium" or "computer usable medium" as used herein refers to any medium that participates in providing instructions to processor 707 for execution. Such a medium may take many forms including, but not limited to, non-volatile media and volatile media. Non-volatile media includes, for example, optical or magnetic disks such as disk drives or tape drives. Volatile media includes dynamic memory such as a random access memory.

Common forms of computer readable media includes, for example, floppy disk, flexible disk, hard disk, magnetic tape, or any other magnetic medium; CD-ROM or any other optical medium; punch cards, paper tape, or any other physical medium with patterns of holes; RAM, PROM, EPROM, FLASH-EPROM, or any other memory chip or cartridge, or any other non-transitory computer readable medium. Such data can be stored, for example, in any form of external data repository 731, which in turn can be formatted into any one or more storage areas, and which can comprise parameterized storage 739 accessible by a key (e.g., filename, table name, block address, offset address, etc.).

Execution of the sequences of instructions to practice certain embodiments of the disclosure is performed by a single instance of the computer system 700. According to certain embodiments of the disclosure, two or more instances of computer system 700 coupled by a communications link 715 (e.g., LAN, PTSN, or wireless network) may perform the sequence of instructions required to practice embodiments of the disclosure using two or more instances of components of computer system 700.

The computer system 700 may transmit and receive messages such as data and/or instructions organized into a data structure (e.g., communications packets 738). The data structure can include program instructions (e.g., application code 703), communicated through communications link 715 and communications interface 714. Received program code may be executed by processor 707 as it is received and/or stored in the shown storage device or in or upon any other non-volatile storage for later execution. Computer system 700 may communicate through a data interface 733 to a database 732 on an external data repository 731. Data items in a database can be accessed using a primary key (e.g., a relational database primary key).

The processing element partition 701 is merely one sample partition. Other partitions can include multiple data processors, and/or multiple communications interfaces, and/or multiple storage devices, etc. within a partition. For example, a partition can bound a multi-core processor (e.g., possibly including embedded or co-located memory), or a partition can bound a computing cluster having plurality of computing elements, any of which computing elements are connected directly or indirectly to a communications link. A first partition can be configured to communicate to a second partition. A particular first partition and particular second partition can be congruent (e.g., in a processing element array) or can be different (e.g., comprising disjoint sets of components).

A module as used herein can be implemented using any mix of any portions of the system memory and any extent of hard-wired circuitry including hard-wired circuitry embodied as a processor 707. Some embodiments include one or more special-purpose hardware components (e.g., power control, logic, sensors, transducers, etc.). A module may include one or more state machines and/or combinational logic used to implement or facilitate the performance characteristics of the system.

Various implementations of the database 732 comprise storage media organized to hold a series of records or files such that individual records or files are accessed using a name or key (e.g., a primary key or a combination of keys and/or query clauses). Such files or records can be brought into and/or stored in volatile or non-volatile memory.

In the foregoing specification, the disclosure has been described with reference to specific embodiments thereof. It will, however, be evident that various modifications and changes may be made thereto without departing from the broader spirit and scope of the disclosure. For example, the above-described process flows are described with reference to a particular ordering of process actions. However, the ordering of many of the described process actions may be changed without affecting the scope or operation of the disclosure. The specification and drawings are, accordingly, to be regarded in an illustrative sense rather than in a restrictive sense.

What is claimed is:

1. A method comprising:
receiving physiological data associated with at least one health condition of an animal subject;
receiving environmental data associated with one or more environment conditions to which the animal subject is or has been exposed, wherein said environmental data comprises at least historical data over a certain period, wherein said certain period is at least one hour;
determining operating parameters for at least one environmental device having variable output based at least partially on at least a portion of physiological data and at least a portion of said historical data, wherein determining the operating parameters comprises at least comparing said at least one physiological data to a baseline measurement and either increasing or decreasing said output depending on whether said at least one physiological data is above or below said baseline, wherein the degree to which the output is increased or decreased depends at least in part on said historical data;

transmitting the set of operating parameters to the at least one environmental device to at least partially control the output to thereby at partially control the at least one health condition; and wherein said environmental condition comprises at least one of temperature, time, time zone, location of the animal, presence of the animal, duration of the presence of the animal, humidity, wind, wind chill, precipitation, barometric pressure, sun rise and sun set, dew point, tides, smog index/air quality, UV index, sound/noise, light exposure, diet, drug intake.

2. The method of claim 1, wherein said environmental device controls said environmental condition.

3. The method of claim 1, wherein said environmental condition comprises at least smog index/air quality.

4. The method of claim 1, wherein said environmental condition comprises at least UV index.

5. The method of claim 1, wherein said environmental condition comprises at least sound/noise.

6. The method of claim 1, wherein said environmental condition comprises at least diet.

7. The method of claim 1, wherein said environmental condition comprises at least drug intake.

8. The method of claim 1, wherein determining the operating parameters comprises comparing the at least a portion of physiological data and the at least a portion of environmental data to one or more predetermined limits and then using logic operators based on the comparison to establish the operating parameters for the at least one environmental device.

9. The method of claim 8, wherein the predetermined limits are established using a learning program.

10. The method of claim 8, wherein the predetermined limits are established by altering the at least one environmental condition and recording the change in the at least one health condition.

11. The method of claim 1, wherein said animal is a human.

12. The method of claim 1, wherein said set of environmental data is obtained at least partially from a wearable.

13. A method comprising:
receiving a set of physiological data associated with at least one health condition of an animal subject;

receiving a set of environmental data associated with one or more environment conditions to which the animal subject is or has been exposed, wherein said set of environmental data comprises at least historical data corresponding to accumulated light exposure of said subject over a certain period, wherein said certain period is at least one hour;

determining a set of operating parameters for at least one environmental device having variable output based at least partially on at least a portion of the set of physiological data and at least a portion of the set of environmental data, and wherein determining the operating parameters comprises determining a change in output of said at least one environmental device based on said at least one physiological data and said accumulated light exposure, wherein determining the operating parameters comprises at least comparing said at least one physiological data to a baseline measurement and either increasing or decreasing said output depending on whether said at least one physiological data is above or below said baseline, wherein the degree to which the output is increased or decreased depends at least in part on said accumulated light exposure;

transmitting the set of operating parameters to the at least one environmental device to at least partially control the output to thereby at partially control the at least one health condition; and wherein said environmental condition comprises at least one of temperature, time, time zone, location of the animal, presence of the animal, duration of the presence of the animal, humidity, wind, wind chill, precipitation, barometric pressure, sun rise and sun set, dew point, tides, smog index/air quality, UV index, sound/noise, light exposure, diet, drug intake.

14. The method of claim 13, wherein said animal is a human.

15. The method of claim 14, wherein said human is a shift worker.

16. The method of claim 13, wherein said set of environmental data is obtained at least partially from a wearable.

17. The method of claim 16, wherein said wearable is a smart watch.

18. The method of claim 11, wherein said human is a shift worker.

19. The method of claim 12, wherein said wearable is a smart watch.

* * * * *